(12) United States Patent
Throckmorton et al.

(10) Patent No.: US 11,998,728 B2
(45) Date of Patent: Jun. 4, 2024

(54) HYBRID GYROSCOPIC SWITCHABLE BLOOD PUMP

(71) Applicant: Drexel University, Philadelphia, PA (US)

(72) Inventors: Amy L. Throckmorton, Cherry Hill, NJ (US); Carson Fox, Philadelphia, PA (US); Harutyun Sarkisyan, Rancho Cordova, CA (US); Steven Chopski, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 677 days.

(21) Appl. No.: 17/143,380

(22) Filed: Jan. 7, 2021

(65) Prior Publication Data

US 2021/0205599 A1    Jul. 8, 2021

Related U.S. Application Data

(60) Provisional application No. 62/958,040, filed on Jan. 7, 2020.

(51) Int. Cl.
| | | |
|---|---|---|
| A61M 60/237 | (2021.01) | |
| A61M 60/178 | (2021.01) | |
| A61M 60/196 | (2021.01) | |
| A61M 60/232 | (2021.01) | |
| A61M 60/489 | (2021.01) | |
| A61M 60/81  | (2021.01) | |
| A61M 60/855 | (2021.01) | |

(52) U.S. Cl.
CPC ........ *A61M 60/178* (2021.01); *A61M 60/196* (2021.01); *A61M 60/232* (2021.01); *A61M 60/237* (2021.01); *A61M 60/489* (2021.01); *A61M 60/81* (2021.01); *A61M 60/855* (2021.01)

(58) Field of Classification Search
CPC .......................... A61M 60/232; A61M 60/237
See application file for complete search history.

(56) References Cited

U.S. PATENT DOCUMENTS

| | | |
|---|---|---|
| 942,952 A   | 12/1909 | Wrather |
| 1,236,204 A | 8/1917  | Norden |
| 2,098,564 A | 11/1937 | Carter et al. |
| 2,174,777 A | 10/1939 | Carter et al. |
| 2,412,481 A | 12/1946 | Summers, Jr. |
| 2,635,469 A | 4/1953  | Summers, Jr. |
| 2,722,126 A | 11/1955 | Summers, Jr. |
| 2,722,127 A | 11/1955 | Summers, Jr. |
| 2,732,721 A | 1/1956  | Summers, Jr. |
| 2,828,629 A | 4/1958  | Summers, Jr. |

(Continued)

*Primary Examiner* — Jacqueline Wozinicki
(74) *Attorney, Agent, or Firm* — Howson & Howson LLP (57) ABSTRACT

A switchable pump device is provided and comprises a pump assembly including first and second pumps each having a separate inlet and outlet, an inner core or shell housing the pump assembly, and an outer shell housing the inner shell and having a pair of openings. The outer shell is interconnected to the inner shell such that the inner shell is movable relative to the outer shell to enable the inlet and outlet of a selected one of the first and second pumps to be aligned with the pair of openings in the outer shell to place the selected one of the first and second pumps in an operational condition while the other of the first and second pumps is positioned in an inoperative condition.

18 Claims, 10 Drawing Sheets

(56) References Cited

U.S. PATENT DOCUMENTS

| | | |
|---|---|---|
| 3,287,982 A | 11/1966 | Hayner et al. |
| 3,430,499 A | 3/1969 | Craig |
| 3,814,348 A | 6/1974 | Johnson |
| 4,623,350 A | 11/1986 | Lapetre et al. |
| 4,961,352 A | 10/1990 | Downer et al. |
| 5,263,979 A * | 11/1993 | Isoyama ............. A61M 60/554 623/3.13 |
| 5,824,070 A | 10/1998 | Jarvik |
| 5,938,412 A | 8/1999 | Izraelev |
| 5,947,406 A | 9/1999 | Burlingame |
| 6,045,326 A | 4/2000 | Lecat |
| 9,095,428 B2 | 8/2015 | Kabir et al. |
| 9,689,403 B2 | 6/2017 | Fang et al. |
| 9,919,085 B2 | 3/2018 | Throckmorton et al. |
| 9,970,437 B2 | 5/2018 | Yuan |
| 10,814,053 B2 | 10/2020 | Throckmorton et al. |
| 2005/0220636 A1* | 10/2005 | Henein ............... A61M 60/873 417/423.1 |
| 2016/0256619 A1* | 9/2016 | Throckmorton .... A61M 60/196 |
| 2021/0236801 A1* | 8/2021 | Sarkisyan ........... A61M 60/126 |

* cited by examiner

HYBRID GYROSCOPIC SWITCHABLE BLOOD PUMP

CROSS REFERENCE TO RELATED APPLICATIONS

This application claims the benefit under 35 USC § 119(e) of U.S. Provisional Patent Application No. 62/958,040, filed Jan. 7, 2020.

BACKGROUND

Heart transplantation is the definitive treatment option for heart failure in pediatric patients and adults, and the limited number of donor organs necessitates the usage and development of blood pump technology for children and adults. Blood pump technologies, specifically for children, continue to lag behind those developed for adults. Although adult-intended devices have been utilized in children, the operation of these pumps at off-design pressures and flows increases the potential for irregular blood flow, contributing to harmful hemolysis and dangerous thrombosis. In addition, there is no medical device that supports the dysfunctional states of pediatric heart failure and the anatomic and physiological heterogeneity of cardiac defects in pediatric patients.

Accordingly, a device with the versatility of providing mechanical circulatory support from infancy to adolescence or from childhood to adulthood, allowing for growth and development with long-term support is desired.

BRIEF DESCRIPTION OF THE DRAWINGS

Various features of the embodiments described in the following detailed description can be more fully appreciated when considered with reference to the accompanying figures, wherein the same numbers refer to the same elements.

DETAILED DESCRIPTION

For simplicity and illustrative purposes, principles of embodiments are described below by referring primarily to examples thereof. In the following description, numerous specific details are set forth to provide a thorough understanding of the embodiments. It will be apparent to one of ordinary skill in the art that the embodiments may be practiced without limitation to these specific details. In some instances, well known methods and structures have not been described in detail so as not to unnecessarily obscure the embodiments.

According to embodiments disclosed herein, a medical device is provided that can function as a right-sided ventricular assist device, a left-sided ventricular assist device, or as a total artificial heart for partial or full cardiovascular support of patients. The implantable medical device integrates two continuous flow blood pumps that are designed on the basis of anatomic and physiologic cardiovascular requirements for infants, children, adolescents, and adults with heart failure.

According to at least some embodiments, the medical device comprises a switchable pump device 10 including a pump assembly 12 providing an axial flow blood pump 14 and a centrifugal pump 16. The central hub space of the centrifugal pump 16, which is normally underutilized space, is occupied by the axial flow pump 14, such that the impellers for both the axial flow blood pump 14 and the centrifugal pump 16 share a common axis of rotation. For example, see the disclosure provided by U.S. Pat. No. 9,919,085 B2, which is hereby incorporated by reference. Thus, the impeller of the centrifugal blood pump 16 rotates around the axial flow pump domain. The small size of the switchable pump device 10 makes it appropriate for younger and older patient populations with heart failure.

More specifically with respect to one contemplated pump assembly 12 and as disclosed in the U.S. Pat. No. 9,919,085, the axial flow pump 14 is integrated with the centrifugal flow pump 16 such that the axial flow pump 14 extends through a central opening of the annular impeller of the centrifugal flow pump 16. A casing of the pump assembly 12 has an outer housing and an integral hollow support shaft extending therethrough. The pump casing may define a first flow path for circulation within the outer housing about an exterior of the hollow support shaft and a separate second flow path for circulation extending within the hollow support shaft.

The annular impeller of the centrifugal flow pump 16 is housed within the outer housing of the casing and rotates about the hollow support shaft thereby providing the centrifugal flow pump 16 in the first flow path within the device 10. The annular impeller may have a generally ring-shaped body having a central opening and an upper surface with raised vanes for directing the flow of blood in a radial direction during operation and rotation of the annular impeller.

For purposes of providing a centrifugal flow pump 16, the outer housing includes an inlet tube and a volute chamber having a discharge outlet. With this arrangement, blood returning from circulation is received within the inlet tube and enters the outer housing adjacent an exterior surface of the support shaft with minimal flow disturbance or elevated shear stresses which may cause thrombogenesis. The blood is forced to flow in radial direction by rotation of the annular impeller into the volute chamber where it is collected and discharged via an outlet into circulation at a desired pressure and flow rate.

The inlet tube extends adjacent and slightly above the surface of the annular impeller in a radial direction relative to the annular impeller. In addition, the inlet tube opens into the outer housing adjacent the exterior surface of the hollow support shaft to feed the blood centrally within the centrifugal flow pump 14. Flow in the inlet tube and through the outlet of the volute chamber is generally perpendicular to the flow through the hollow support shaft.

The axial flow impeller is housed within the hollow support shaft of the pump casing for forming the axial flow pump 14 within the second flow path defined within the support shaft. The axial flow impeller may be positioned to extend directly within and through the central opening of the annular impeller of the centrifugal flow pump 16. An axis of rotation of the centrifugal flow annular impeller may also form and be the same as the axis of rotation of the axial flow impeller (i.e., the impellers may share a common axis of rotation).

The second flow path within the hollow support shaft may include various sections that comprise the axial flow pump 14. For instance, the pump 14 may include an inducer section, an impeller housing section, a diffuser section, and a straightener section. The impeller may include blades or vanes providing axial flow of blood through the pump 14 and may be positioned in housing section. The inducer section may provide an inlet for blood returning from circulation, may provide a narrowed flow path adjacent the impeller, and may include a set of stationary vanes for ensuring axial flow of blood into the impeller housing section. The diffuser and straightener sections may also include sets of stationary vanes for diffusing and straightening flow being discharged into circulation at a desired pressure and flow rate.

Accordingly, an annular impeller is housed within the outer housing of the casing for rotation about the hollow support shaft to provide the centrifugal flow pump, and an axial flow impeller is housed within the hollow support shaft of the casing to provide the axial flow pump.

According to embodiments disclosed herein, the above referenced pump assembly 12 having the two pumps, 14 and 16, are internally housed in a separate substantially spherically-shaped inner core or shell 18 which is interconnected to and located within a substantially spherically-shaped outer layer or shell 20 (e.g., in the form of onion layers). See FIGS. 1-4. Shapes other than spherical may also be utilized.

Accordingly, the switchable pump device 10 includes a pair of pumps, 14 and 16, combined into a compact housing provided by inner core 18 and outer shell 20 and provides a single inflow fluid path 22 and a single outflow fluid path 24 for an individual one of the blood pumps 14 and 16. For this purpose, the outer shell 20 includes a pair of openings, 26 and 28, which can be aligned to utilize one of the pumps, 14 or 16. The openings, 26 and 28, of the outer shell 20 may incorporate cannula connections (not shown) that are adapted to link on of the pumps, 14 or 16, of the switchable pump device 10 to the large blood vessels or ventricles of a patient.

Figure 1:
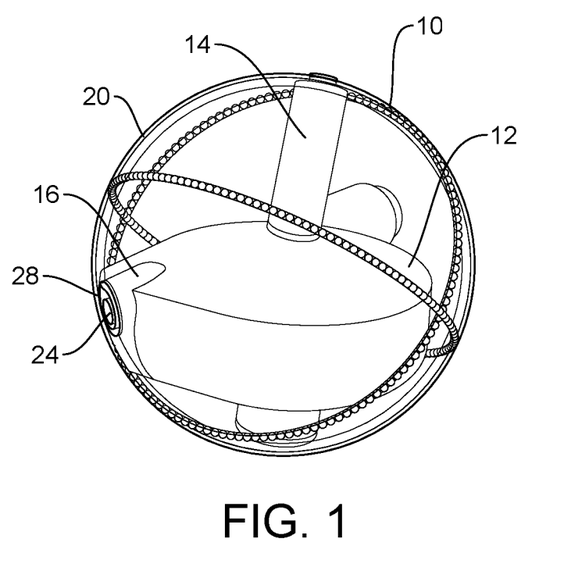
FIG. 1 is a perspective view of a hybrid gyroscopic switchable blood pump in a condition switched to provide a centrifugal blood pump in accordance to an embodiment.
Figure 2:
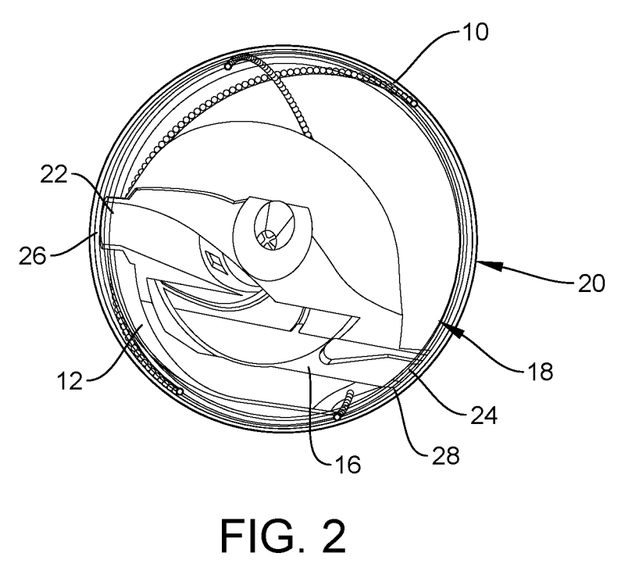
FIG. 2 is a partially cut-away perspective view of the hybrid gyroscopic switchable blood pump of FIG. 1.
Figure 3:
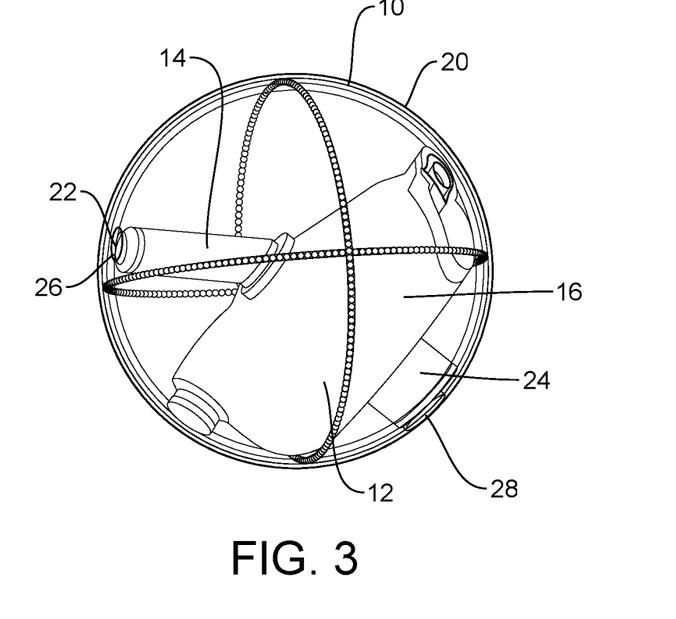
FIG. 3 is a perspective view of a hybrid gyroscopic switchable blood pump in a condition switched to provide an axial-flow blood pump in accordance to an embodiment.
Figure 4:
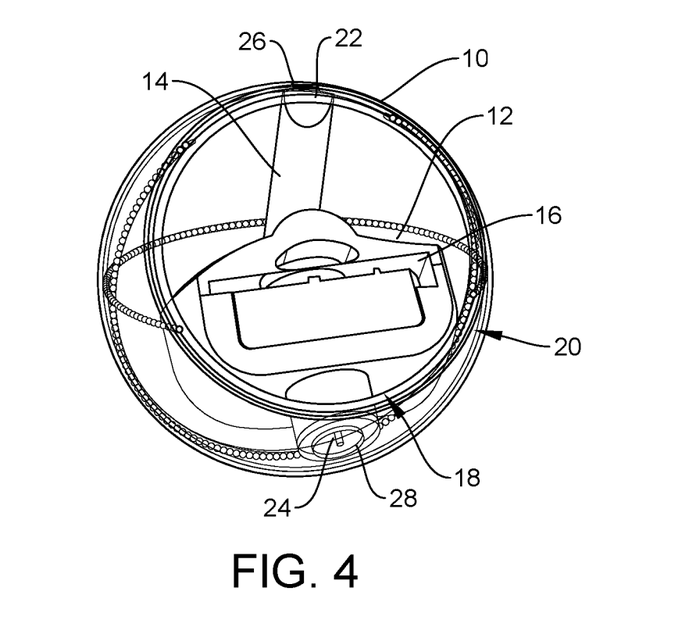
FIG. 4 is a partially cut-away perspective view of the hybrid gyroscopic switchable blood pump of FIG. 3.

By way of example, FIGS. 1 and 2 show the inlet and outlet of the centrifugal pump 16 being aligned with the openings 26 and 28 of the outer shell 20. Thus, in this condition, blood flow through the switchable blood pump 10 is through the centrifugal pump 16 which is in an operational condition with no flow through the axial flow pump 14 which is in a non-operative condition. Conversely, FIGS. 3 and 4 show the inlet and outlet of the axial flow pump 14 being aligned with the openings 26 and 28 of the outer shell 20. Thus, in this condition, blood flow through the switchable blood pump 10 is through the axial flow pump 14 which is in an operational condition with no flow through the centrifugal pump 16 which is in a non-operative condition.

For the above purpose, the switchable pump device 10 is designed in a manner permitting the inner core 18, which houses the pumps, 14 and 16, to rotate internally relative to the outer shell 20, thus enabling a rotational switch from one of the blood pumps, 14 or 16, to the other. This rotation may be similar to that which occurs in a gyroscope.

In use, the outer layer 20 of an implanted switchable pump device 10 is secured, fixed, and directly connected to the blood vessels or ventricles of the patient and thus is stationary relative to the patient, and the inner core 18 housing the pumps, 14 and 16, can be rotated to switch a selected one of the pumps to an operational condition and the other of the pumps into a non-operative condition. This rotation or movement of the inner core 18 relative to the outer shell 20 may be driven by a gyroscopic-based switching mechanism. A gyroscope consists of a rotatable structure and a fixed structure with a connection between the two being provided by gimbal rings or joints that provide movement or deflection of the movable structure when moved out of its normal plane. Such rotation of the movable structure may have 1-, 2-, or 3-degrees of freedom.

Accordingly, rotation of the inner core 18, and thus the pumps, 14 or 16, relative to the outer shell 20 along multiple axes will allow the inlet and outlet of a selected one of the pumps, 14 or 16, to switch into alignment with the openings, 26 and 28, of the outer shell 20, thereby changing the blood pump in active or operational use while the other pump is switched to a non-active or non-operative condition. Such a pump switching method allows a fixed inlet and a fixed outlet provided by the openings, 26 and 28, on the outer shell 20 to switch between connections to the inlets and outlets of the pumps, 14 and 16. Accordingly, multiple pumps may be placed inside the inner core or shell to allow for a variety of different pump choices in consideration of patient-specific needs and various disease states that are being treated (e.g. moderate-to-failure of the heart, right-sided or left-sided support). Various pump geometries and impeller designs may be selected for purposes of realizing an appropriate device for a specific patient at any instance in time in which the device 10 is implanted within the patient.

Thus, this medical device allows for usage of the axial flow blood pump 14 and then a switch to the centrifugal flow blood pump 16, or vice versa. A device with this versatility is able to provide mechanical circulatory support from infancy to adolescence or from childhood to adulthood, allowing for growth and development with long-term support. By way of example, the axial and centrifugal blood pumps, 14 and 16, may be designed to generate 1-7 L/min of flow with pressure generations of 1-180 mmHg at 1500-15000 RPM.

Figure 22:
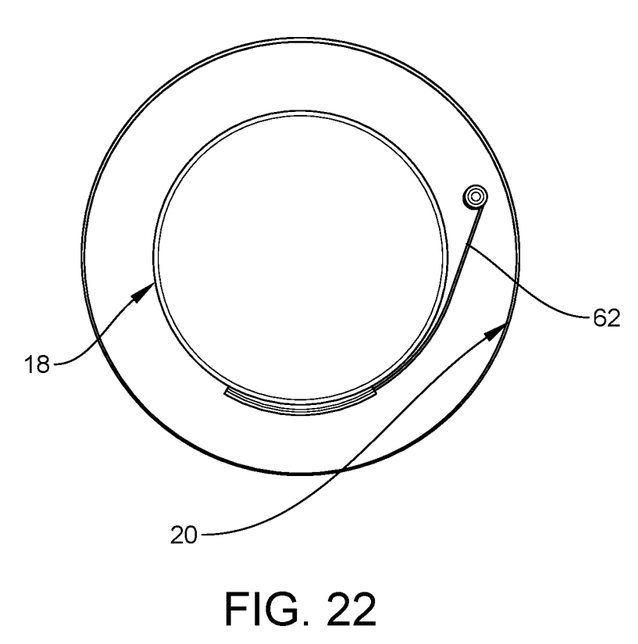
FIGS. 22 and 23 are views of a cable spooling gyroscopic rotational mechanism for switching between pumps of a hybrid gyroscopic switchable blood pump in accordance to an embodiment.
Figure 23:
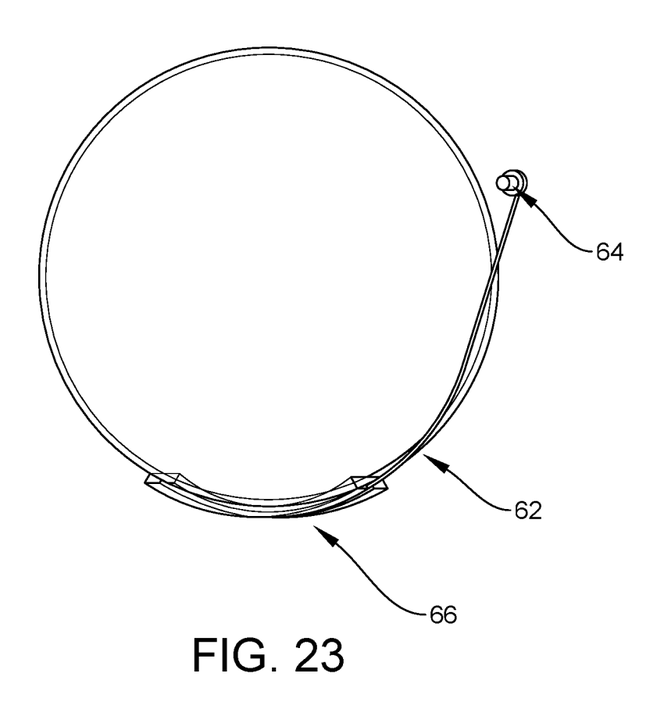

As stated above, the switchable pump device 10 may include a gyroscopic rotation mechanism (for instance, see the various embodiments shown in FIGS. 5-23). Such mechanisms enable rotation between the inner core 18 and outer shell 20 such that the blood flow path through the device 10 can be switched from one of the above referenced blood pumps, 14 or 16, to the other. Merely by way of example, the gyroscopic rotation mechanism may be selected from: a wheel and track mechanism (see FIGS. 5 and 6), a miniature gear system (see FIGS. 7 and 8), a fluid-driven system (see FIGS. 9-11), a spring-loaded mechanism with or without a locking pin (see FIGS. 12 and 13), electromagnetic bearings and couplings (see FIGS. 14-19), a pin and slot mechanism (see FIGS. 20 and 21), and a cable or wire spooling mechanism (see FIGS. 22-23).

For gyroscope support, the axis of rotation may be defined with slides, ball bearings and axial points, and gimbal joints used as a means to rotate the inner core 18 housing the pumps, 14 and 16, mounted therein for realignment to the inlet and outlet connections via openings 26 and 28, provided by the outer shell 20 for cannulae.

The implantable medical device according to embodiments is of a compact size and yet makes it possible to switch from using one type (i.e., axial flow) of blood pump to another (centrifugal flow). Leveraging the unique combination of the axial and centrifugal pumps ensures a compact overall size unlike other mechanical circulatory support devices.

The device provides a novel cannulation strategy in that it permits an exchange between two blood pumps without surgery by reusing the existing inflow and outflow cannulae. Thus, the device can be utilized to provide versatile long-term mechanical support and enables clinicians to provide a viable therapeutic alterative to mechanically support patients from infancy to adolescence and from childhood to adulthood because a switch can be made from the axial flow blood pump to the centrifugal blood pump as the patient ages or grows and develops. This concept and medical device can function as a right-sided ventricular assist device, left-sided ventricular assist device, or could form part of a total artificial heart for partial or full cardiovascular support of patients. The pumps may be usable with multiple different impeller designs so that the optimal impeller design may be selected prior to implantation for a patient's specific needs and disease state.

The outer shell 20 may be substantially spherical and include the pair of spaced apart openings, 26 and 28, in which a pair of cannulae can be extended to interconnect the blood pump that is switched into an operational state to the large blood vessels or ventricles of the patient through which blood flows and is pumped through the implanted device. Since there is a limit to the range of angles between the inlet and the outlet cannulae of the two blood pumps, 14 and 16, in the inner core 18 of the medical device 10, the openings, 26 and 28, in the outer shell 20 are preferably oriented at an angle from each other within a range of 75° to 180°.

Various different gyroscopic rotational mechanisms may be integrated into the switchable pump device 10 for causing rotation of the inner core or shell 18 relative to the outer shell 20. The gyroscopic rotational mechanisms that will enable a switch from one pump to another may include: a wheel and track mechanism, a miniature gear system, a fluid driven system, a spring-loaded mechanism with or without a locking pin, electromagnetic bearings and couplings, a pin and slot design, and a cable or wire spooling concept.

Figure 5:
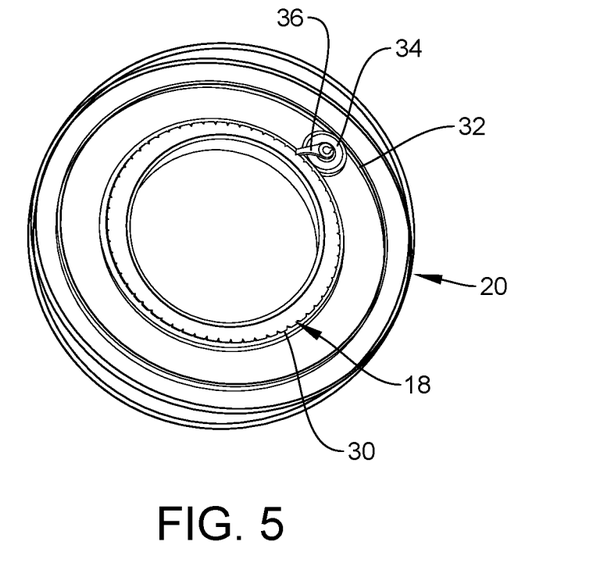
FIGS. 5 and 6 are perspective and plan views, respectively, of a wheel and track gyroscopic rotational mechanism for switching between pumps of a hybrid gyroscopic switchable blood pump in accordance to an embodiment.
Figure 6:
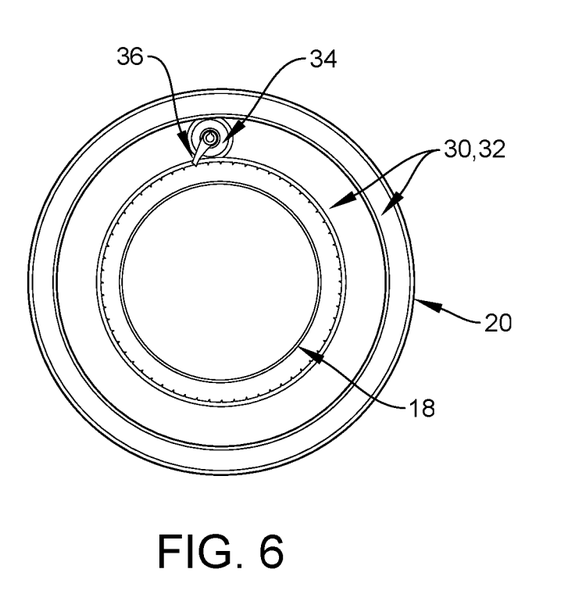

A wheel and track mechanism is shown in FIGS. 5 and 6 and may be used to provide rotation of the inner core 18 via use of one or two tracks or grooves, 30 and 32, in which a wheel 34 is forced to follow without slippage. Either or both of the tracks, 30 and 32, may curve or provide an arcuate path along the circumference of the outside surface of the inner core 18 and the inside surface of outer shell 20 as shown in FIGS. 5 and 6. The wheel 34 is located and captured between the two tracks, 30 and 32, and drives movement of the inner core 18 relative to the outer shell 20. The wheel 34 may be caused to rotate by means of a shaft (not shown) connected to an electric motor (not shown) or by the use of a key (not shown) used to turn the wheel 34. A ratchet mechanism 36 may be included with the wheel 34 to prevent rollback of the wheel 34 relative to the tracks, 30 and 32.

Figure 7:
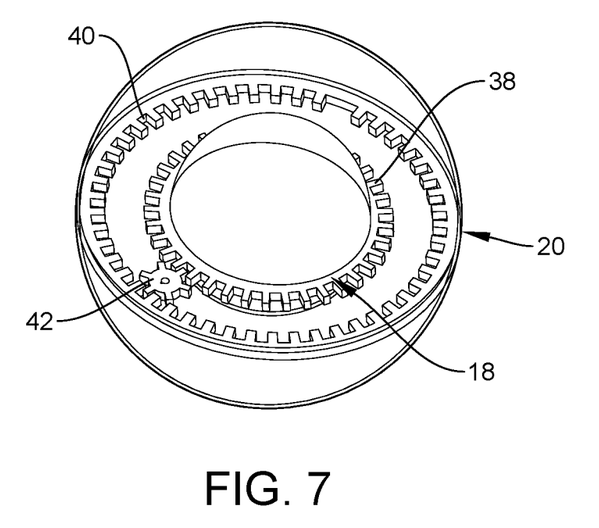
FIGS. 7 and 8 are perspective and plan views, respectively, of a gear system gyroscopic rotational mechanism for switching between pumps of a hybrid gyroscopic switchable blood pump in accordance to an embodiment.
Figure 8:
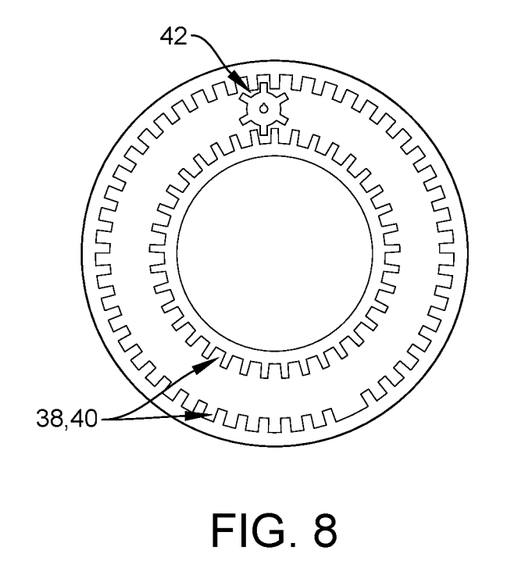

As an alternative, a miniature gear system as shown in FIGS. 7 and 8 including a gear train, or rack and pinion mechanism, may be used to induce rotation of the inner core 18 relative to the fixed outer shell 20. Two racks, 38 and 40, having a set of gear teeth curve along the circumference of the outside of the inner core 18 and the inside of outer shell 20. A pinion gear 42 is located between the two racks, 38 and 40, and provides movement of the racks, 38 and 40, relative to each other. The pinion gear 42 may be operated by means of a second gear (not shown) that is connected to an electric motor (not shown) or by the use of a key (not shown) to turn the gear. A ratchet stop (not shown) may be included to prevent the reversal of the gears.

Figure 9:
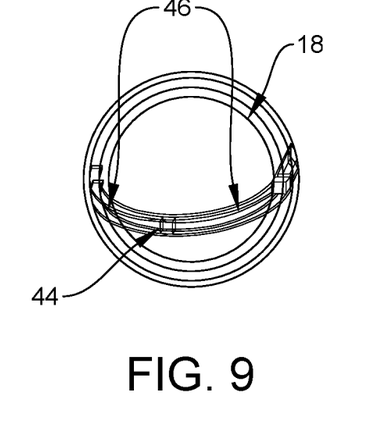
FIGS. 9-11 are front, plan, and side views, respectively, of a fluid-driven gyroscopic rotational mechanism for switching between pumps of a hybrid gyroscopic switchable blood pump in accordance to an embodiment.
Figure 10:
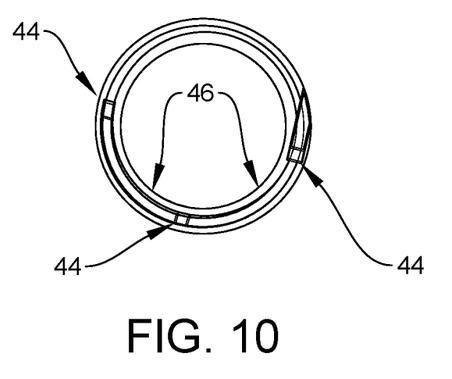
Figure 11:
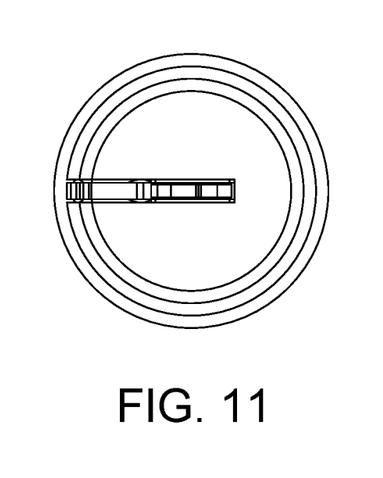

Another alternative is provided by a fluid driven system utilizing pressure created with a liquid, gas, polymer, or expanding colloid. A gyroscopic mechanism of rotation may be facilitated by a continuous fluid from an integrated hydraulic system, or creation of either from reacting reagents. An expanding colloid or other partially suspend solid, liquid, or gaseous suspension may also be used. Either of these mechanism can be used to drive rotation of the inner core 18 relative to the outer shell 20, for instance, as shown in FIGS. 9-11. Pressurized fluid or an expanding colloid may be used to exert force onto a surface. If this surface is a block piston or lever 44 enclosed in a groove or canal 46, pressure is built up until the block piston 44 moves along the canal 46. Conversely, a pressurized fluid or an expanding colloid may be encapsulated inside of the inner core 18. Release of this substance through puncture or rupture of the container or reservoir may be used to cause rotation of the inner shell 18 through loss of pressure. In addition, laparoscopic intervention in a cardiac catheterization laboratory may also trigger rotation by penetrating through a thick polymer or colloid material. The inner core 18 could then be rotated relative to the outer shell 20 and locked in place.

Figure 12:
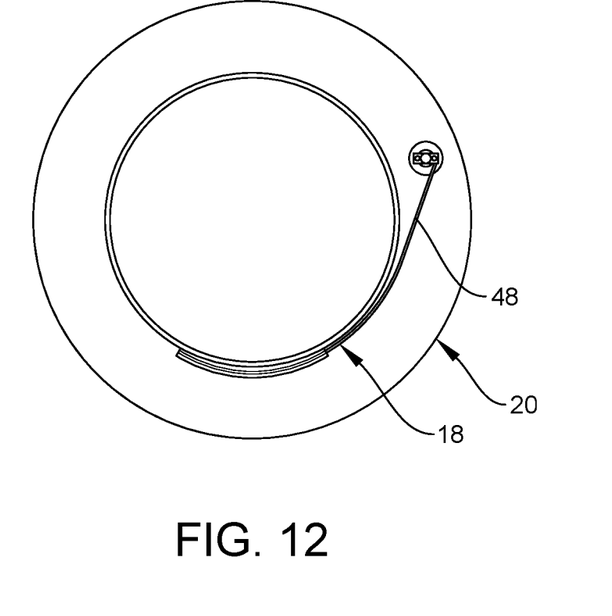
FIGS. 12 and 13 are views of a spring-loaded gyroscopic rotational mechanism for switching between pumps of a hybrid gyroscopic switchable blood pump in accordance to an embodiment.
Figure 13:
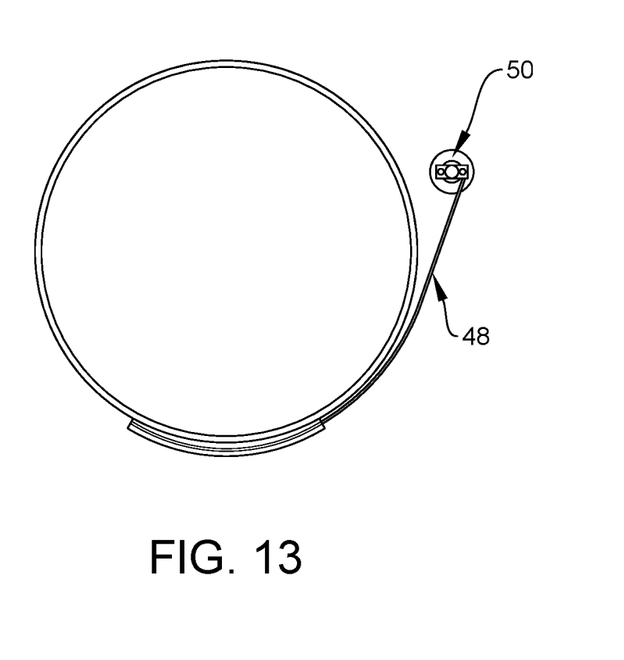
Figure 14:
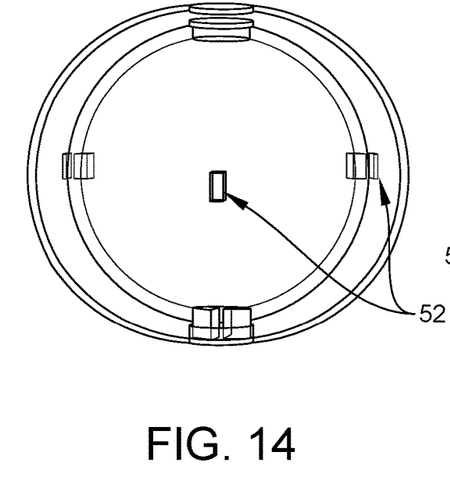
FIGS. 14-19 are views of electromagnetic bearing and coupling gyroscopic rotational mechanisms for switching between pumps of a hybrid gyroscopic switchable blood pump in accordance to embodiments.
Figure 15:
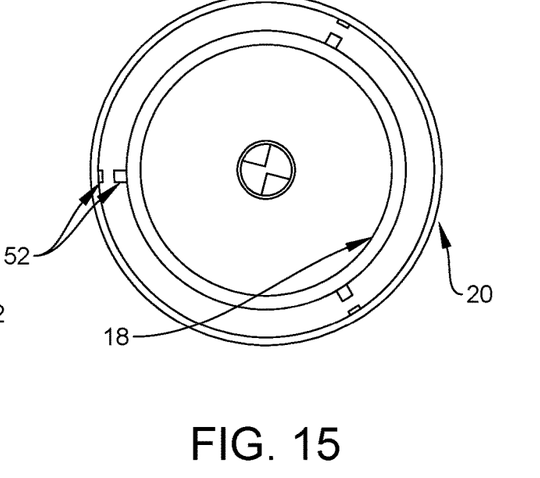
Figure 16:
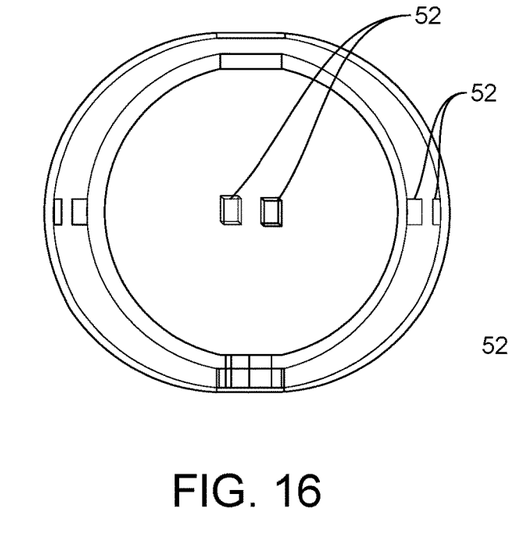
Figure 17:
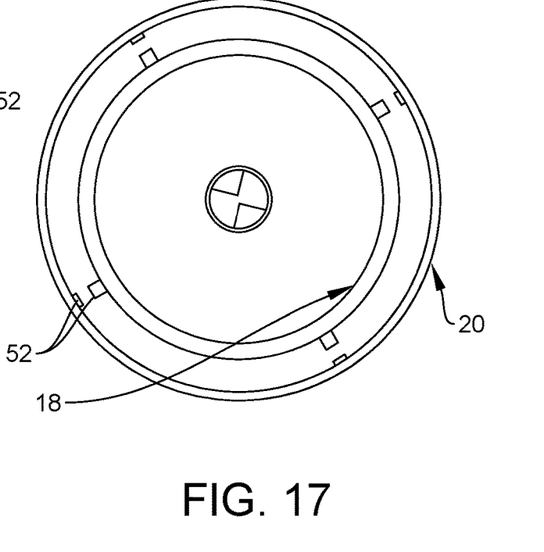
Figure 18:
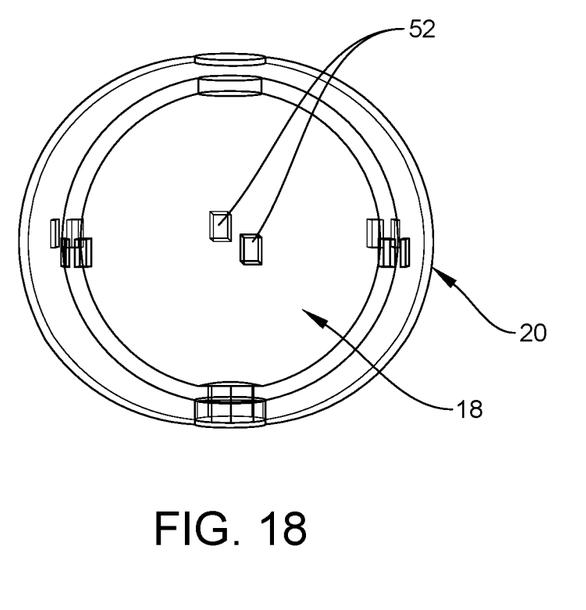
Figure 19:
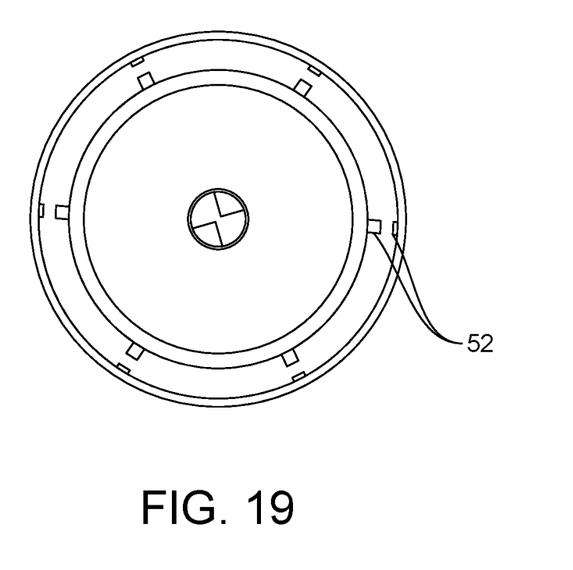

As another alternative, a spring-loaded mechanism as shown in FIGS. 12 and 13 could be incorporated between the inner core 18 and outer shell 20 such that a spring 48 provides tension between the two with a secondary support (not shown) using ball bearings in a groove to provide a direction of rotation. A locking pin 50 may be used to keep the springs in tension until such time that the locking pin is removed and the springs are able to contract and move the inner core 18 to a final fixed position relative to the outer shell 20.

As a further alternative, electromagnetic bearings and couplings may be used. Since the axial and centrifugal blood pumps may have rotors that are levitated in a magnetic field by incorporating power and drive technology, this can be leveraged to further use magnetic bearings to induce inner core rotation while keeping the outer shell fixed. These could include a set of passive or active magnets 52 that are mounted to the surface of the inner core 18 and outer shell 20. Current flow will produce a magnetic flux and interactions of the magnets 52 will induce rotation of the inner core 18. This could be due to passive north-south pole attraction or repulsion, or as active magnets that function similar to a brushless DC motor or as a linear actuator. The number of electromagnets 52 that may be used, for example, may be three (see FIGS. 14 and 15), four (see FIGS. 16 and 17) or six (see FIGS. 18 and 19) to cause rotation of the outer shell 20 through repulsive magnetic force. Curvilinear rails (not shown) with embedded magnets in a carrier may be used to propel the carried along the electromagnetically-innervated rail.

Figure 20:
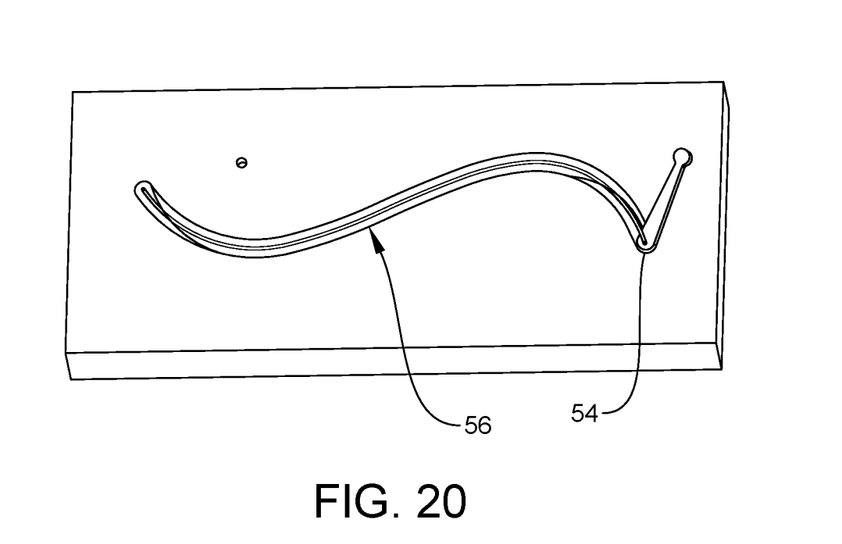
FIGS. 20 and 21 are views of a pin and slot gyroscopic rotational mechanism for switching between pumps of a hybrid gyroscopic switchable blood pump in accordance to an embodiment.
Figure 21:
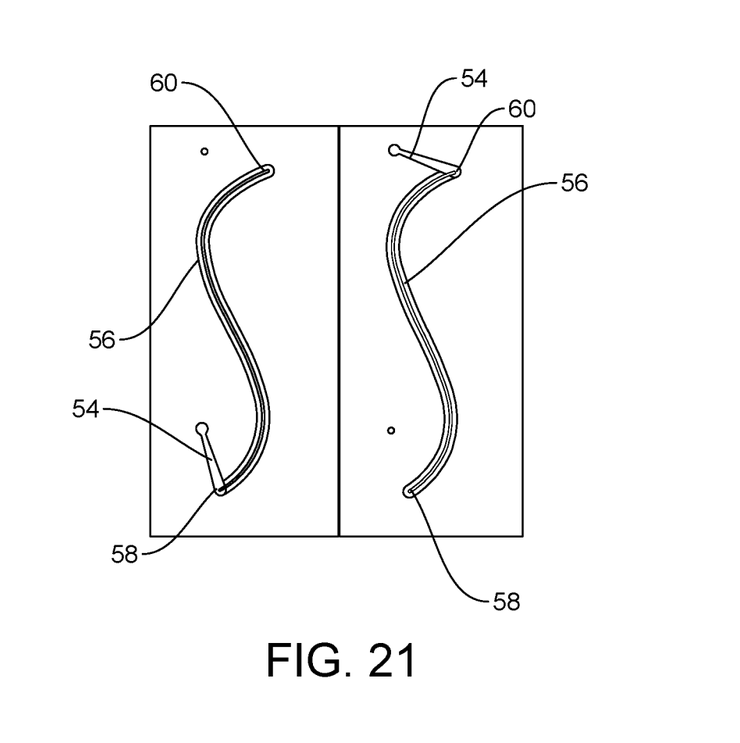

A further alternative is to use a pin and slot mechanism to provide a guided path for the rotation of the inner core 18 relative the outer shell 20, for instance, as shown in FIGS. 20 and 21. A pin 54 may be a locking type pin that restricts motion of the pin 54 from one end of a slot 56 to the opposite end of the slot 56. The length of the slot 56 will provide the degree and direction of curvature that the inner and outer shells, 18 and 20, twist around each other along two axes. By way of example, this may be guided via magnetic propulsion. The sliding mechanism has two end positions, 58 and 60. Both shells, 18 and 20, may have magnets (not shown) placed that can be activated at different times and points to allow the outer shell 20 to follow the slot 56 on the inner core 18 (or vice versa) and thereby precisely dictate the change of relative positions of the inner core 18 to the outer shell 20.

Yet a further alternative is provided by a cable or wire spooling system. See FIGS. 22 and 23. A cable or wire 62 may be used to provide rotation of the inner or outer shells, 18 and 20, such that the cable or wire 62 is wrapped around a spool or mandrel 64. A miniature system of pulleys (not shown) may be used to redirect the force of the cable or wire 62 to the spool 64. Additionally, a groove or casing 66 may be used to redirect the cable or wire 62. When tension is provided to the cable or wire 62, the spool 64 is permitted to rotate. A pulley wheel (not shown) may include a ratchet mechanism (not shown) to prevent the pulley from reversing direction. The wire or cable 62 may be substituted with a one-way locking mechanism with or without teeth or grooves in a thin strap to prevent reversal.

The hybrid gyroscopic switchable blood pump device 10 described above provides many advantages over existing medical devices that are used to provide mechanical circulatory support to pediatric and adult patients. The above disclosed device incorporates two pumps within an inner core, and the inner core is able to rotate usage from one device to the other in vivo and as implanted to support patients with heart failure.

According to embodiments a method of switching blood pumps is also provided. The method includes a process step of activating a switching mechanism of a switchable pump device 10 that is implanted within a patient. The switchable pump device 10 is connected via cannulas to large blood vessels or ventricles of the patient, and upon activating the switching mechanism, a first pump of the switchable pump device 10 which is in an operational condition is moved and replaced in vivo with a second pump of the switchable pump device 10. The switchable pump device 10 may be the medical device as described above. For instance, it may include a pump assembly with first and second pumps each having a separate inlet and outlet, an inner core or shell housing the pump assembly, and an outer shell housing the inner shell and having a pair of openings. As described above, the outer shell is interconnected to the inner shell such that the inner shell is movable or rotatable relative to the outer shell to enable the inlet and outlet of one of the first and second pumps to be aligned with the pair of openings in the outer shell to place the selected pump in an operational condition while the other pump is placed in an inoperative condition.

While the principles of the invention have been described above in connection with specific devices, systems, and/or methods, it is to be clearly understood that this description is made only by way of example and not as limitation. For instance, while an implantable blood pump is described above, the disclosed device may be used in any mechanical circulatory support system. In addition, the pump design may also be used for other medical and non-medical purposes.

One of ordinary skill in the art will appreciate that various modifications and changes can be made without departing from the scope of the claims below. Accordingly, the specification and figures are to be regarded in an illustrative rather than a restrictive sense, and all such modifications are intended to be included within the scope of the present invention.

We claim:

1. A switchable pump device, comprising:
   a pump assembly including first and second pumps each having a separate inlet and outlet;
   an inner shell housing said pump assembly; and
   an outer shell housing said inner shell and having a pair of openings, said outer shell being interconnected to said inner shell such that said inner shell is movable relative to said outer shell to enable the inlet and outlet of one of said first and second pumps to be aligned with said pair of openings in said outer shell to place said one of said first and second pumps in an operational condition while the other of said first and second pumps is placed in an inoperative condition.

2. The switchable pump device according to claim 1, wherein at least one of said first and second pumps is a centrifugal pump.

3. The switchable pump device according to claim 1, wherein at least one of said first and second pumps is an axial flow pump.

4. The switchable pump device according to claim 1, wherein the first and second pumps include a centrifugal pump and an axial flow pump.

5. The switchable pump device according to claim 1, wherein the switchable pump device is a blood pump, an implantable blood pump, a right or left ventricular assist device, or part of a total artificial heart.

6. The switchable pump device according to claim 1, wherein said pump assembly comprises:
   a pump casing including an outer housing and an integral hollow support shaft extending therethrough, said casing defining a first flow path of said first pump within the outer housing about an exterior of said hollow support shaft and a separate second flow path of said second pump extending within said hollow support shaft;
   said first pump being a centrifugal flow pump and having an annular impeller housed within said outer housing of said casing for rotation about said hollow support shaft; and
   said second pump being an axial flow pump and having an axial flow impeller housed within said hollow support shaft of said casing.

7. The switchable pump device according to claim 1, wherein said inner shell is rotatable within and relative to said outer shell.

8. The switchable pump device according to claim 7, wherein said outer shell is interconnected to said inner shell with a gyroscopic-based switching mechanism.

9. The switchable pump device according to claim 8, wherein said gyroscopic-based switching mechanism includes a wheel located within opposite grooves formed in the inner and outer shells.

10. The switchable pump device according to claim 8, wherein said gyroscopic-based switching mechanism comprises a gear system including a rack and pinion.

11. The switchable pump device according to claim 8, wherein said gyroscopic-based switching mechanism comprises a fluid driven system including a fluid path extending between said inner and outer shells interconnected to a source of fluid.

12. The switchable pump device according to claim 8, wherein said gyroscopic-based switching mechanism comprises a spring.

13. The switchable pump device according to claim 8, wherein said gyroscopic-based switching mechanism comprises magnets.

14. The switchable pump device according to claim 8, wherein said gyroscopic-based switching mechanism comprises a pin that is configured to travel within a slot.

15. The switchable pump device according to claim 8, wherein said gyroscopic-based switching mechanism comprises a cable.

16. A method of switching between two types of blood pumps, comprising a step of activating a switching mechanism of a switchable pump device implanted within a patient, the switchable pump device including a first pump in an operational condition and a second pump in an inoperative condition and being connected via cannulas to large blood vessels or ventricles of the patient, and upon activating the switching mechanism, the first pump of the switchable pump device is switched in vivo to the inoperative condition and the second pump of the switchable pump device is switched in vivo to the operational condition, wherein the switchable pump device comprises a pump assembly including the first and second pumps each having a separate inlet and outlet, an inner shell housing said pump assembly, and an outer shell housing said inner shell and having a pair of openings, said outer shell being interconnected to said inner shell such that said inner shell is movable relative to said outer shell during said activating step to enable the inlet and outlet of the second pump to be aligned with said pair of openings in said outer shell to place the second pump in the operational condition while the first pump is placed in the inoperative condition.

17. The method according to claim 16, wherein the first and second pumps include an axial flow pump and a centrifugal pump.

18. The method according to claim 16, wherein during said activating step said inner shell is rotated within and relative to said outer shell.

* * * * *